United States Patent [19]
Yoshida et al.

[11] Patent Number: 6,036,730
[45] Date of Patent: Mar. 14, 2000

[54] HAIRDYE COMPOSITIONS

[75] Inventors: Masashi Yoshida; Kazunobu Suzuki, both of Yokohama, Japan

[73] Assignee: Shiseido Company, Ltd., Tokyo, Japan

[21] Appl. No.: 09/147,037

[22] PCT Filed: Jan. 21, 1998

[86] PCT No.: PCT/JP98/00219

§ 371 Date: Sep. 16, 1998

§ 102(e) Date: Sep. 16, 1998

[87] PCT Pub. No.: WO98/31330

PCT Pub. Date: Jul. 23, 1998

[30] Foreign Application Priority Data

Jan. 21, 1997 [JP] Japan .................................. 9-022061
Feb. 10, 1997 [JP] Japan .................................. 9-041586

[51] Int. Cl.⁷ ...................................... A61K 7/13
[52] U.S. Cl. ....................................... 8/406; 8/405; 8/561
[58] Field of Search .......................... 8/405, 406, 428, 8/429, 561, 649

[56] References Cited

U.S. PATENT DOCUMENTS 5,466,283 11/1995 Kondo et al. .................... 106/25 R

FOREIGN PATENT DOCUMENTS

| 1-279819 | 11/1989 | Japan . |
| 6-74283 | 9/1994 | Japan . |
| 8-268848 | 10/1996 | Japan . |
| 97/49376 | 12/1997 | WIPO . |

*Primary Examiner*—Caroline D. Liott
*Attorney, Agent, or Firm*—Townsend & Banta

[57] ABSTRACT

Hair dye compositions containing acidic hair dyes and oxidation hair dyes, as well as a method of dyeing the hair using the aforementioned hair dyes, are provided. The hair dye compositions of the present invention can be obtained by blending succinoglycan, which is a type of polysaccharide derived from microorganisms, into the hair dye composition containing the oxidation or acidic hair dyes.

5 Claims, No Drawings

HAIRDYE COMPOSITIONS

FIELD OF THE INVENTION

The present invention belongs in general to the technical field related to a hair dye composition, particularly a acidic hair dye composition and an oxidation hair dye composition.

BACKGROUND OF THE INVENTION

Hair dyes for dyeing hair are widely used as, for example, "gray hair dyes" and "fashion dyes". These hair dyes are generally classified as "temporary hair dyes" which are for temporary hair dyeing, "semi-permanent hair dyes" which give a semi-permanent hair dyeing effect and "permanent hair dyes" which give a permanent hair dyeing effect.

These hair dyes, as a matter of course, contain a coloring agent to dye the hair to a desired color. For this coloring agent, an "acidic dye" which exhibits the best hair dyeing effect in the acidic pH region is one of the most preferable because it has superior safety as a coloring agent for hair dye. Particularly for the coloring agent for "semi-permanent hair dyes" which are designed to have a semi-permanent hair dyeing effect, azo type acidic dyes are mainly used. Therefore, there is a great need for acidic dyes for hair dyes.

When using "acidic hair dyes" which have this acidic dye for the coloring agent, the pH has to be adjusted to the strongly acidic region of 1.5–4.5 and a thickener is commonly added to keep this strongly acidic hair dye from dripping and touching something other than the hair.

However, the selection of the thickeners which can be used in this strongly acidic pH region is fairly limited and even the thickeners which are said to be usable in the strongly acidic region are not necessarily satisfactory on the whole as thickeners to be added to hair dyes.

That is, an example of the main thickeners currently used in acidic hair dyes is xanthan gum (Japanese examined patent publication Tokko Hei 2-32253). A system in which bentonite and/or cross-linked sodium polyacrylate is used in addition to xanthan gum for improved performance (Tokko Hei 2-32253) has also been used.

However, conventionally known hair dyes with added xanthan gum, while they are certainly stable around pH 4.0–5.0, their viscosity significantly changes, resulting in a stability problem, in the strongly acidic region of pH 1.5–4.0. Also, it cannot be denied that the flowability is poor and, when scooped up on a hand and applied to the head, it tends to drip off as a lump and spreading it onto the hair tends to be difficult. Also, it gives a sticky feeling when used and hence is not satisfactory in terms of sensation of touch at the time of use.

Because of this, a system in which bentonite and or cross-linked sodium polyacrylate is used in addition to xanthan gum was discovered to improve the aforementioned flowability. However, there still is a problem in stability and also a problem has arisen in that it takes a long time and effort to wash it off after use.

Among the aforementioned "permanent hair dyes", "oxidation hair dyes" which develop colors by making an oxidizing agent act on an oxidation dye have a particularly permanent effect and have a bleaching effect as well to make the color tone of the hair brighter than it was originally. Because of this, they are among the most commonly used hair dyes.

This oxidation hair dye usually takes the form of the two formulation type comprising the formulation (I) which contains the oxidation dye and the formulation (II) which contains the oxidizing agent (the powder type is a one formulation type because it utilizes air oxidation). In the two formulation type hair dye, formulation (I) is used to make the low molecular weight oxidation dye penetrate into the hair and then formulation (II) is used to initiate oxidation polymerization of the oxidation dye in the hair and on the hair surface so as to produce pigments and complete the dyeing process.

However, although the oxidation hair dyes conventionally used have a superior hair dyeing ability, they have a problem in that when they are used the hair is damaged, loses moisture and gloss and combing becomes difficult. Furthermore, although they are called "permanent hair dyes", they have a tendency to gradually fade through exposure to sunlight and/or the use of shampoo. Therefore, an oxidation hair dye with superior fastness is desired. Various investigations have been conducted so far to make up for these shortcomings, but none has been recognized as producing a satisfactory result.

For example, an attempt was made to solve these problems by blending dextrin pullulan, which is a polysaccharide, into the oxidation hair dye (Japanese examined patent publication Tokko Hei 4-3206). However, although the use of dextrin pullulan did provide good dye-affinity, the fastness against sunlight and or washing was not sufficient and the problem of "damaged hair" was not completely solved. Also, dextrin pullulan caused a problem in stability over time depending on the oxidation hair dye system. It must be said therefore that dextrin pullulan had some unsuitable characteristics for blending in an oxidation hair dye composition.

Therefore, the object of the present invention is to provide a hair dye composition which has superior characteristics compared to the aforementioned conventional technology. Specifically, the following can be listed as the objects:

The first object is to provide an acidic hair dye composition which is stable even in the strongly acidic pH region (pH 1.5–4.0), has a high flowability, has superior feeling at the time of use and is thickened in such a way that washing-off after use does not require too much time and effort.

The second object is to provide an oxidation hair dye composition which has significantly improved dyeability and improved fastness against sunlight and/or washing, reduces hair damage down to very little, gives gloss to the hair and has superior stability over time.

DISCLOSURE OF THE INVENTION

The inventors conducted earnest research to achieve these objects and discovered that a hair dye composition to which succinoglycan is added exhibits the desired superior characteristics, thus completing the present invention.

To be specific, firstly, the inventors discovered that an acidic hair dye composition to which succinoglycan is added exhibits a high flowability and stability in the aforementioned strongly acidic region regardless of the type of the acidic dye, has superior feeling at the time of use and washes off easily after use. Also, the inventors discovered that it has superior dyeability and homogeneity of dyeing as well as superior color retention.

Secondly, the inventors discovered that an oxidation hair dye composition to which succinoglycan is added exhibits significantly improved dyeability and improved fastness against sunlight and/or washing, reduces hair damage down to very little and gives gloss to the hair. Furthermore, the inventors also discovered that such an oxidation hair dye had significantly superior stability over time compared with the oxidation hair dyes containing the aforementioned dextrin pullulan.

That is, the present invention is an invention which provides hair dye compositions, in particular an acidic hair dye composition and an oxidation hair dye composition.

In the present invention, a "acidic hair dye composition" means a hair dye composition which uses for the coloring agent an "acidic dye" which exhibits its best dyeing effect in the acidic region (pH 4.0 or lower). While this "acidic hair dye composition" is primarily used as a semi-permanent hair dye, it can be used either for "gray hair dyeing" or "fashion dyeing".

In this invention, as described above, an "oxidation hair dye" refers to a hair dye in which the dyeing to the desired color of the hair is done by making an oxidizing agent act on the blended oxidation dye to cause oxidation polymerization. It can either be a two formulation type or a one formulation type. Also, for the oxidation dye, either a dye precursor alone or a combination of a dye precursor and a coupler can be used.

THE BEST MODES OF THE EMBODIMENTS

Embodiments of the present invention are described below.

In the present specifications, the hair dye compositions pertaining to the present invention are referred to as the "hair dye compositions of the present invention". This concept includes both the "acidic hair dye composition of the present invention" which means the acidic hair dye composition pertaining to the present invention and the "oxidation hair dye composition of the present invention" which means the oxidation hair dye composition pertaining to the present invention.

Succinoglycan which is blended into the hair dye composition of the present invention is a type of polysaccharide derived from microorganisms. It refers to a polysaccharide derived from microorganisms which contains sugar units derived from galactose and glucose and also units derived from succinic acid, pyruvic acid and optionally acetic acid as well as salts of these acids.

More specifically, succinoglycan is a water soluble polymer with a structural formula with an average molecular weight of approximately 6 millions or less, containing galactose units (1 part), glucose units (7 parts), succinic acid units (0.8 parts) and pyruvic acid units (1 part) as well as optional acetic acid units.

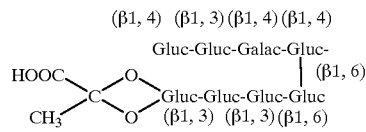

(In this formula, Gluc denotes a glucose unit and Galac denotes a galactose unit. The indications in parentheses denote the bonding types between the sugar units. For example, (β1, 4) denotes a β1–4 bond.)

Examples of the microorganisms which supply this succinoglycan include bacteria of genus Pseudomonas, genus Rhizobium, genus Alcaligenes or genus Agrobacterium. Among these bacteria, Agrobacterium Tumefaciens I-736 (entrusted to Collection Nationale de Culture des Microorganismes (CNCM) on Mar. 1, 1988 according to the Budapest treaty and publicly available as item number I-736) is particularly preferable as a source of succinoglycan.

Succinoglycan can be prepared by cultivating these microorganisms in a culture medium.

More specifically, succinoglycan can be prepared by cultivating the aforementioned microorganisms in a culture medium which contains carbon sources such as glucose, sucrose and hydrolyzed starch; organic nitrogen sources such as casein, caseinate, vegetable powder, yeast extract, corn steep liquor (CSL); inorganic salts such as sulfate, phosphate or carbonate of metals; and optionally trace minerals.

In general, this cultivation should preferably be carried out at a pressure of 1–4 bars and a temperature of 25–35° C. under aerobic conditions. The pH of the culture medium should preferably be 5–9, more preferably 6–8.

After completion of the culture and the heat treatment of the culture medium, succinoglycan can be isolated by continuously exposing the medium to an organic solvent such as isopropanol. When isolating succinoglycan, it should preferably be filtered, centrifuged, pressurized and dried to obtain succinoglycan to be blended into the hair dye composition of the present invention.

Succinoglycan thus prepared can be blended into the hair dye composition of the present invention as it is. Decomposed products of it obtained by acid decomposition, alkali decomposition, enzyme decomposition, ultrasonic treatment, etc. can also be blended in.

The amount of succinoglycan to be blended into the hair dye composition of the present invention is generally in the range of 0.001 wt % or more and 50.0 wt % or less, preferably 0.005 wt % or more and 10.0 wt % or less, and more preferably 0.1 wt % or more and 5.0 wt % or less, of the total composition. (In the hair dye composition of the present invention, the weight of the composition which is the basis for the weight percent indication is defined as: (1) the weight of the formulation (I) or (II), whichever contains the indicated ingredient when the hair dye composition is used in a two formulation type hair dye, and (2) the weight of the total hair dye when the hair dye composition is used in a one formulation type hair dye. Here after this definition will be used.)

It is not preferable if the amount of succinoglycan blended in is less than 0.001 wt % of the total acidic hair dye composition because then succinoglycan's function as a thickener would not be fully exhibited. It would not be preferable to blend more than 50.0 wt % either because then the flowability of the hair dye composition tends to decrease.

When the hair dye composition of the present invention is an oxidation hair dye composition the amount of succinoglycan is also generally in the range of 0.001 wt % or more and 50.0 wt % or less, preferably 0.005 wt % or more and 10.0 wt % or less, and more preferably 0.1 wt % or more and 5.0 wt % or less of the total composition.

It is not preferable if the amount of succinoglycan blended is less than 0.01 wt % of the total oxidation hair dye composition, because then the hair dyeing effect and the hair damage prevention effect are more difficult to achieve. It would not be preferable to blend more than 50.0 wt % either, because then the improvement in the effect would not be comparable to the increase in the amount.

Under normal conditions, succinoglycan exhibits rheological characteristics comparable to xanthan gum which is widely used as a thickener. Furthermore, it is quite stable even at severe temperatures, pH and salt concentrations.

The hair dye composition of the present invention in which this succinoglycan is blended is a hair dye composition with excellent characteristics, whether it is an acidic hair dye composition or an oxidation hair dye composition.

These characteristics are described below by dividing them into (A) characteristics of the acidic hair dye composition and (B) characteristics of the oxidation hair dye composition.

(A) Acidic Hair Dye Composition of the Present Invention

The acidic hair dye composition of the present invention is an acidic hair dye composition with superior characteristics as described below.

The acidic hair dye composition of the present invention does not exhibit decomposition behaviors such as changes in the viscosity, coloration, degradation of the smell, etc. and is stable even when pH and salt concentrations change over time. Also, the acidic hair dye composition of the present invention has thixotropy and therefore has superior extensibility, applicability, dyeing homogeneity and dyeability even when the system is given enough viscosity to prevent dripping.

It also exhibits superior color retention. Surprisingly, the acidic hair dye composition of the present invention, compared with conventional acidic hair dye compositions, is not sticky and gives a refreshing feeling at the time of use. Also, it washes off easily after use.

By additionally blending silicones into the acidic hair dye composition of the present invention, the feeling of use of this acidic hair dye composition can be significantly improved. Because of this, particularly when the acidic hair dye composition of the present invention takes the form of a one formulation type, it can take a form of a rinse plus hair dye agent after shampooing.

Examples of silicones which can be blended into the acidic hair dye composition of the present invention include dimethyl polysiloxane, methylphenyl polysiloxane, polyether modified polysiloxane, amino modified polysiloxane, fluorine modified polysiloxane and alcohol modified polysiloxane.

The amount of these silicones blended into the acidic hair dye composition of the present invention is preferably 0.01 wt % or more and 5.0 wt % or less of the total composition. If the amount to be blended is less than 0.01 wt % of the total composition, then the expected improvement of the feeling of use cannot be obtained. It is not preferable to blend more than 5.0 wt % either because then stickiness arises and the feeling of use of the acidic hair dye composition of the present invention tends to deteriorate.

In addition to succinoglycan and these silicones, other ingredients usually used in acidic hair dyes can be added to the acidic hair dye composition of the present invention as long as they do not hinder the expected effect of the present invention. That is, for example, acidic dyes, alcohol, organic solvents and acid for pH adjustment can be added as necessary.

For the acidic dye which is blended into the acidic hair dye composition of the present invention, very effective examples are legal pigments listed in the "ordinance stipulating tar colors which can be used in medicinal drugs and such" which do not exhibit harmful actions on a human body and are allowed to be used as coloring medicinal drugs, quasi-drugs and cosmetics. The preferable amount to be blended in is 0.01 wt % or more and 2.0 wt % or less of the total composition. When the hair dye composition is used as a rinse plus acidic hair dye, the amount should preferably be 0.01 wt % or more and 0.1 wt % or less.

Examples of the organic solvents blended into the acidic hair dye composition of the present invention include aliphatic alcohols, aromatic alcohols and polyhydric alcohols, ring ketones and ethers. Specific examples include n-butyl alcohol, sec-butyl alcohol, cyclohexanol, benzyl alcohol, 2-phenoxy ethanol, phenyl ethanol, tetrahydrofurfuryl alcohol, N-methylpyrrolidone, ethylene carbonate, methyl cellusolve, ethyl cellusolve, butyl cellusolve, methyl carbitol, ethyl carbinol, 1,3-butylene glycol, dipropylene glycol and propylene glycol. At least one type of organic solvent chosen from among these groups of organic solvents is blended in the amount of 5.0 wt % or more and 50.0 wt % or less of the total composition.

Examples of the acid for pH adjustment to be blended into the acidic hair dye composition of the present invention include organic acids such as citric acid, malic acid, acetic acid, lactic acid, oxalic acid, tartaric acid, formic acid, levulinic acid and glycolic acid as well as inorganic acids such as phosphoric acid, hydrochloric acid, sulfuric acid and nitric acid. The amount to be blended into the system is such that the pH of the system falls in the strongly acidic region of 1.5–4.0, more preferably 1.5–3.0.

In addition to these, humectants such as glycerine, 1,3-butylene glycol, hexylene glycol, propylene glycol, dipropylene glycol, polyethylene glycol, chondroitin sulfate, hyaluronate, diglycerine, sorbitol, maltitol, pyrolidone-carboxylic acid, lactose and oligo sugar can be blended into the acidic hair dye composition of the present invention.

Also, oil based ingredients such as lanolin, squalane, liquid paraffin, vaseline, higher fatty acid, triglyceride, ester oil, etc. can be blended into the acidic hair dye composition of the present invention.

Amphiphilic substances and or surfactants, as diffusing and solubilizing agents, can be blended into the acidic hair dye composition of the present invention.

For example, stearyltrimethyl ammonium chloride, glycerine monostearate, etc. can be blended into the acidic hair dye composition of the present invention.

Also, thickeners such as lauric acid diethanolamide, carboxymethyl cellulose, carboxyvinyl polymer, hydroxyethyl cellulose, hydroxypropyl cellulose, methyl cellulose, xanthan gum, carrageenan, alginate, pectin, farceran, gum arabic, gutch gum, karaya gum, gum tragacanth, agar powder, bentonite and cross-linked polyacrylate can be blended into the acidic hair dye composition of the present invention. However, these thickeners have to be blended in with care lest addition of them affects the expected effect of the present invention.

Also, hydrolyzed proteins such as hydrolyzed collagen, hydrolyzed keratin, hydrolyzed silk protein, hydrolyzed elastin and hydrolyzed soybean protein as well as their quarternarized salts can be added to the acidic hair dye composition of the present invention.

Also, surfactants which are generally blended into an acidic hair dye composition can be blended in, even if the purpose is not diffusion or solubilization as described above.

Also, polyoxyethylene type surfactants such as polyoxyethylene alkyl ether, polyoxyethylene fatty acid ester, polyoxyethylene polyhydric alcohol fatty acid partial ester and polyoxyethylene hardened castor oil derivatives, alkylpolyglycosides such as octylpolyglycoside, polyglycerine type surfactants such as polyglycerine fatty acid ester and polyglycerine alkyl ether, sugar alcohol ethers such as maltitol hydroxyalkyl ether and sorbitol alkyl ether, non-ionic surfactants such as fatty acid diethanol amide, anion surfactants such as higher fatty acid salts, phosphoric esters, alkylsulfates, polyoxyethylene alkylsulfate and alkylsulfuric ester salts, cation surfactants such as amino acids, alkyltrimethyl ammonium salts, dialkyldimethylammonium salts and alkyldimethylamine oxide, and other surfactants can be blended as necessary into the acidic hair dye composition of the present invention.

Also, in addition to the aforementioned "organic solvents", alcohols such as ethanol, propanol and isopropanol as well as higher alcohols such as 2-ethylhexyl alcohol, 2-hexyldecyl alcohol, 2-decyltetradecyl alcohol, isostearyl alcohol, cetostearyl alcohol, lauryl alcohol, oleyl alcohol, myristyl alcohol, palmityl alcohol, stearyl alcohol and cetyl alcohol can be blended into the acidic hair dye composition of the present invention.

Also, preservatives and sequestering agents such as phenacetin, hydroxyethanediphosphonic acid and its salt, EDTA and its salt, parabens and stannates, cation polymers such as poly (dimethylallylammonium halide) type cationic polymers, cation polymers which are a condensation product of taroylamine obtained from polyethylene glycol, epichlorohydrine, propylene amine and beef tallow fatty acid, cation polymers which are a condensation product of cocoyl amine obtained from polyethylene glycol, epichlorohydrine, propylene amine and coconut oil fat, vinylpyrolidone-dimethylaminomethacrylate copolymer type cation polymers and cellulose ether type cation polymers containing a quarternarized nitrogen, as well as pH adjustment agents, perfumes, various active ingredients and water can be blended into the hair dye composition of the present invention.

The aforementioned ingredients are blended into the acidic hair dye composition of the present invention as necessary. However, ingredients which can be blended in are not limited to these ingredients.

The acidic hair dye composition of the present invention can be used in any form that an acidic hair dye composition can commonly take. For example, it can take the form of a semi-permanent hair dye, temporary hair dye, hair dye for gray hair, hair dye for fashion dyeing, hair dye for rinse plus dyeing, etc.

It can also prepared as a formulation suitable for any desired form. For example, it can take the form of a liquid, cream, gel, spray, mousse, stick, one formulation type, two formulation type, etc.

(B) Oxidation Hair Dye Composition of the Present Invention

The oxidation hair dye composition of the present invention is an oxidation hair dye composition with superior characteristics as described below.

Remarkably, the oxidation hair dye composition of the present invention does not exhibit decomposition behaviors such as changes in the viscosity, aggravation of coloration, degradation of the smell, etc. and is stable even when pH and salt concentrations change over time.

Also amazing is the fact that the oxidation hair dye composition of the present invention exhibits superior fastness, prevents hair damage and gives sufficient gloss to the hair. That is, succinoglycan blended into the oxidation hair dye composition of the present invention is adsorbed between the cuticles and has chemical interaction with keratin protein to form a relatively fast thin film with a three dimensional structure on the hair surface, thus producing the effects of preventing hair damage and improving the hair itself.

Also, the oxidation hair dye composition of the present invention has thixotropy and therefore has superior extensibility, applicability, dyeing homogeneity and dyeability even when the system is given enough viscosity to prevent dripping.

Furthermore, blending polypeptide and or its derivative, in addition to the aforementioned succinoglycan, into the oxidation hair dye composition of the present invention improves the expected effects of the present invention even further. Examples of the polypeptide and/or its derivative to be blended in addition to succinoglycan into the oxidation hair dye composition of the present invention include decomposed natural proteins such as hydrolyzed collagen and hydrolyzed keratin.

The amount of these polypeptides and/or their derivatives to be blended into the oxidation hair dye composition of the present invention is preferably 0.01 or more and 20.0 or less when the weight of succinoglycan blended into the oxidation hair dye composition of the present invention is 1.

As described above, an oxidation hair dye usually takes the form of the two formulation type comprising formulation (I) which contains an oxidation dye and formulation (II) which contains the oxidizing agent. In the present invention, succinoglycan can be blended into either formulation (I) or formulation (II) which are components of the two formulation type. The present invention is also applicable to oxidation hair dyes of the one formulation type.

Therefore, the oxidation hair dye composition of the present invention can take the form of succinoglycan blended into formulation (I), formulation (II), or formulations (I) and (II) of a two formulation type oxidation hair dye, or into a one formulation type oxidation hair dye.

In addition to the aforementioned essential ingredients, other ingredients usually blended into oxidation hair dyes can also be blended into the oxidation hair dye composition of the present invention within the range which does not affect the expected effects of the present invention.

Examples of the oxidation dye precursor to be blended into formulation (I) in the two formulation type include phenylene diamines, amino phenols, toluilenediamines, amino nitrophenols, diamino pyridines and their salts.

Usually, the amount of these oxidation dye precursors blended into the oxidation hair dye composition of the present invention is approximately 0.01 wt % or more and 10.0 wt % or less.

Couplers such as resorcinol, meta-amino phenol, meta-phenylene diamine can also be blended along with the corresponding oxidation dye precursor.

Formulation (I) can additionally contain surfactants such as polyoxyethylene alkylether salt and polyoxyethylene alkylamine fatty acid amide, humectants such as glycerine and propylene glycol, oil-based ingredients such as lanolin and liquid paraffin, stabilizers such as sulfites and ascorbic acid, thickeners such as carboxymethyl cellulose and carboxyvinyl polymer, alkaline agents such as ammonia, monoethanolamine, sodium hydroxide and potassium hydroxide, as well as higher alcohols and perfumes.

For the oxidizing agent in formulation (II), hydrogen peroxide is usually used. However, formulation (II) can also contain stabilizers such as terpinal and sodium stannate, fats and oils such as paraffin, as well as higher alcohols, surfactants, acids, pH adjusting agents and perfumes.

When using such a two formulation type oxidation hair dye composition of the present invention, formulation (I) and formulation (II) are mixed together immediately before use and then used for hair dyeing for 10–30 minutes.

Also, the one formulation type oxidation hair dye can contain, in addition to the aforementioned essential ingredients, 2,4-diaminophenol sulfate, stearyltrimethylammonium-triethanolamine chloride, ammonium thioglycolate, propylene diglycol, LPG (gas), etc.

Specific forms of the hair dye composition of the present invention, including both the acidic hair dye composition of the present invention and the oxidation hair dye composition, are disclosed in the examples below.

EXAMPLES

The present invention is described more specifically by referring to the examples below. However, the present invention is not limited to these examples.

[Preparation example]
Preparation of Succinoglycan

Succinoglycan was prepared according to the method disclosed in Tokko Hei 6-74283.

That is, fermentation was conducted using Agrobacterium Tumefaciens I-736 in a culture medium with the composition described below. That is, Agrobacterium Tumefaciens I-736 was inoculated in this culture medium and agitation culturing at 400 rpm using a Ruston (registered trademark) type agitator at a temperature of 28° C. was carried out in a 20-liter Biolaffite (registered trademark) vessel with a usage capacity of 15 liters. The medium was exposed to air at an air flow rate of 825 liters/hour. After 90 hours of agitation culturing, which amounted to consumption of all or virtually all of the sucrose, a heteropolysaccharide was obtained in the amount of 66 wt % of the weight of sucrose used. The viscosity of the fermented solution, measured by using a Brookfield LTV (registered trademark) viscometer with a No. 4 cylinder spindle at 30 rpm, was 6,800 Pa-second.

Succinoglycan was recovered from 2 kg of the aforementioned fermented solution after 30 minutes of heat treatment at 90° C. That is, 2,300 ml of isopropyl alcohol was added to the heat treated fermented solution and 150 g of sodium sulfate was added to cause precipitation. The fiber from this precipitate was dehydrated twice using 1,200 ml of isopropyl alcohol. This dehydrated fiber was then pressurized, torn to pieces, and dried in an oven at 85° C. The obtained dried substance was crushed and separated by sifting. Cream color succinoglycan powder was thus obtained.

Composition of the Culture Medium

|  | wt % in the culture medium |
|---|---|
| CSL (corn steep liquor) | 11.0 |
| $K_2HPO_4$ | 4.0 |
| $MSO_4—7H_2O$ | 0.5 |
| Sucrose | 25.0 |
| Ion exchanged water | Balance |

Succinoglycan obtained as described above was used in the following examples.

(A) Examples in Which the Hair Dye Composition of the Present Invention is an Acidic Hair Dye Composition

[Evaluation of the Acidic Hair Dye Composition]

The evaluation of the acidic hair dye compositions prepared by the following recipes was carried out by means of 1) stability testing, 2) hair dyeing dripping testing and 3) application ease (stickiness at the time of application) and washing off testing.

Stability Testing

Each hair dye composition was stored at 0° C., room temperature, M1 cycle (temperature changed between 45° C. and −5° C. over one month cycle) and 50° C. for one month and the pH and viscosity of the system was measured to evaluate the stability.

Hair Dyeing/Dripping Testing

A panel of 20 people used each hair dye composition and evaluated spreadability on the hair, applicability, homogeneity of dyeing and dripping.

Application Ease (Stickiness at the Time of Application) and Washing Off Testing A panel of 20 people used each hair dye composition and evaluated the degree of stickiness at the time of application to hair on the head and the degree of ease of washing off the applied hair dye composition.

Example A1

Acidic Hair Dye

|  |  | Blend ratio [wt % of the total composition (this applies to ratios hereafter)] |
|---|---|---|
| (1) | Black 401 | 0.2 |
| (2) | Purple 401 | 0.3 |
| (3) | Yellow 4 | 0.3 |
| (4) | Benzyl alcohol | 4.0 |
| (5) | Succinoglycan | 2.0 |
| (6) | N-methyl pyrolidone | 11.0 |
| (7) | Citric acid (this is used to adjust the pH to 2.5) | 4.0 |
| (8) | Hydrolyzed soy protein | 0.1 |
| (9) | Perfume | Appropriate amount |
| (10) | Ion exchanged water | Balance |

<Preparation Method>

Succinoglycan and hydrolyzed soy protein were added to a mixture of N-methyl pyrolidone and benzyl alcohol and ion exchanged water was added to prepare viscous liquid. Dyes black 401, purple 401 and yellow 4 were added to this viscous solution and citric acid was used to adjust the pH of the system to 2.5 to obtain a homogeneous viscous solution.

In a similar manner, a acidic hair dye composition (Comparative example A1) was prepared using the recipe of the acidic hair dye of the aforementioned Example A1 except for the fact that 2.0 wt % of xanthan gum was used instead of succinoglycan (blend ratios of other ingredients are the same as in the recipe of Example A1 and pH was adjusted to 2.5). Also, a acidic hair dye composition (Comparative example A2) was prepared using the recipe of the acidic hair dye of the aforementioned Example A1 except for the fact that xanthan gum, bentonite and cross-linked sodium polyacrylate were used instead of succinoglycan (the actual recipe is shown below).

[Comparative A2]

|  |  | Blend ratio |
|---|---|---|
| (1) | Black 401 | 0.2 |
| (2) | Purple 401 | 0.3 |
| (3) | Yellow 4 | 0.3 |
| (4) | Benzyl alcohol | 5.0 |
| (5) | Xanthan gum | 1.0 |
| (6) | Cross-linked sodium polyacrylate | 0.5 |
| (7) | N-methyl pyrolidone | 10.0 |
| (8) | Bentonite | 0.5 |
| (9) | Citric acid (this is used to adjust the pH to 2.5) | 4.0 |
| (10) | Hydrolyzed soy protein | 0.1 |
| (11) | Perfume | Appropriate amount |
| (12) | Ion exchanged water | Balance |

The aforementioned tests were conducted on Example A1 and Comparative examples A1 and A2.

Stability Testing

The results of the stability testing (changes in the viscosity after one month) for Example A1 and Comparative examples A1 and A2 are shown in Table 1.

TABLE 1

| Storage temperature | 0° C. | Room temperature | 50° C. | M1 cycle |
|---|---|---|---|---|
| Example A1 (pH 2.5) | ⊚ | ⊚ | ⊚ | ⊚ |
| Comparative example A1 (pH 2.5) | ⊚ | ⊚ | X | o |
| Comparative example A2 (pH 2.5) | o | o | X | o |

Note) In this table:
⊚: No change in viscosity observed.
o: A change in viscosity is observed which is within the acceptable range for a hair dye.
X: A significant change in viscosity was observed which exceeds the acceptable range for a hair dye.

While the acidic hair dye composition of Example A1 exhibited no change in viscosity when stored in the aforementioned temperature conditions, the acidic hair dye compositions of Comparative examples A1 and A2 exhibited viscosity changes after the M1 cycle and also at 50° C. over time. In particular, a significant change in viscosity was observed at 50° C.

For the acidic hair dye composition of Example A1, the pH immediately following preparation and the pH after storage in each of these temperature conditions were virtually the same.

These results indicate that the acidic hair dye composition of the present invention has superior pH stability, chemical stability and viscosity stability compared with the conventional acidic hair dye composition.

Hair Dyeing/Dripping Testing

The results of the hair dyeing dripping testing on the compositions for an acidic hair dye of Example A1 and Comparative examples A1 and A2 are shown in Table 2 (stability and spreadability) and Table 3 (dyeability and homogeneous dyeing).

TABLE 2

| Evaluation | a | b | c | d |
|---|---|---|---|---|
| Example A1 | 20 | 0 | 0 | 0 |
| Comparative example A1 | 18 | 2 | 0 | 0 |
| Comparative example A2 | 15 | 1 | 3 | 1 | a: No lumps; easy to spread.
b: Not much dripping or lumps; easy to spread.
c: Some dripping and lumps are observed; hard to spread.
d: Dripping and lumps are observed; hard to spread.

TABLE 3

| Evaluation | a | b | c | d | ΔE 5 minutes | ΔE 10 minutes | ΔE 15 minutes | ΔE 20 minutes |
|---|---|---|---|---|---|---|---|---|
| Example A1 | 20 | 0 | 0 | 0 | 37.5 | 40.5 | 44.0 | 44.5 |
| Comparative example A1 | 18 | 1 | 1 | 0 | 34.0 | 38.5 | 40.5 | 40.5 |
| Comparative example A2 | 16 | 2 | 1 | 1 | 34.0 | 38.0 | 40.5 | 40.5 | a: Homogeneously dyed with no unevenness.
b: Somewhat homogeneously dyed with no unevenness.
c: Some unevenness is observed; inhomogeneous.
d: Unevenness is observed; inhomogeneous.

ΔE (color difference between before and after dyeing: dyeing conditions: 30° C. dyeing time 5–20 minutes. Measurement is made after shampooing twice and rinsing once. A large Δ E indicates that dyeability is high and the color retention is good.)

Table 2 and Table 3 indicate that the acidic hair dye composition of the present invention exhibits no dripping, is easier to spread, has superior dyeability, and dyes more homogeneously compared with the conventional compositions for acidic hair dyes.

Application Ease and Washing Off Testing

The results of the application ease and washing off testing conducted on the acidic hair dye compositions of Example A1, Comparative example A1 and Comparative example A2 are shown in Table 4. Evaluation of the application ease and washing off is based on the following criteria.

Evaluation of Application Ease

⊚: No stickiness was observed at the time of application (the number of panelists who reported stickiness was four or less).
o: Some degree of stickiness was observed at the time of application, but it was within the range which is allowed for a hair dye (the number of panelists who reported stickiness was five to eight).
x: Stickiness was significant enough to be outside of the allowable range for a hair dye (the number of panelists who reported stickiness was nine or more).

Evaluation of Ease of Washing Off

⊚: Washed off well (the number of panelists who reported poor washing off was four or less).
o: There was some problem in washing off, but it was within the range which is allowed for a hair dye (the number of panelists who reported poor washing off was five to eight).
x: Washing off was significant enough to be outside of the allowable range for a hair dye (the number of panelists who reported poor washing off was nine or more).

TABLE 4

|  | Example A1 | Comparative example A1 | Comparative example A2 |
|---|---|---|---|
| Evaluation of application ease |  |  |  |
| Evaluation of ease of washing off |  | X | X |

The results shown in Table 4 indicate that the acidic hair dye composition of the present invention has improved application ease and is very easy to wash off compared with conventional products.

The following are the compositions for an acidic hair dye from various recipes shown as Examples. Each of the aforementioned tests were conducted on the acidic hair dye composition of each Example. All Examples were significantly superior to corresponding Comparative examples which, just as described above, used xanthan gum or xanthan gum, bentonite and cross-linked sodium polyacrylate instead of succinoglycan.

Example A2
Acidic Hair Dye (2)

|      |                              | Blend ratio        |
| ---- | ---------------------------- | ------------------ |
| (1)  | Black 401                    | 0.2                |
| (2)  | Purple 401                   | 0.3                |
| (3)  | Yellow 4                     | 0.1                |
| (4)  | Benzyl alcohol               | 5.0                |
| (5)  | Succinoglycan                | 2.0                |
| (6)  | Xanthan gum                  | 1.5                |
| (7)  | Cross-linked sodium polyacrylate | 0.2            |
| (8)  | 1,3-butylene glycol          | 10.0               |
| (9)  | Hydrolyzed collagen          | 0.2                |
| (10) | Citric acid                  | 4.0                |
| (11) | Perfume                      | Appropriate amount |
| (12) | Ion exchanged water          | Balance            |

The acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

Example A3
Acidic Hair Dye (3)

|      |                     | Blend ratio        |
| ---- | ------------------- | ------------------ |
| (1)  | Black 401           | 0.2                |
| (2)  | Purple 401          | 0.3                |
| (3)  | Yellow 4            | 0.1                |
| (4)  | 2-phenoxy ethanol   | 5.0                |
| (5)  | Octyl polyglycoside | 1.0                |
| (6)  | Succinoglycan       | 2.5                |
| (7)  | Bentonite           | 1.7                |
| (8)  | Dipropylene glycol  | 12.0               |
| (9)  | Citric acid         | 3.0                |
| (10) | Hydrolyzed keratin  | 0.1                |
| (11) | Perfume             | Appropriate amount |
| (12) | Ion exchanged water | Balance            |

The acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

Example A4
Acidic Hair Dye (4)

|      |                                          | Blend ratio |
| ---- | ---------------------------------------- | ----------- |
| (1)  | Black 401                                | 0.2         |
| (2)  | Purple 401                               | 0.3         |
| (3)  | Yellow 4                                 | 0.1         |
| (4)  | Benzyl alcohol                           | 5.0         |
| (5)  | Succinoglycan                            | 2.0         |
| (6)  | Tamarind gum                             | 2.5         |
| (7)  | Bentonite                                | 3.2         |
| (8)  | Dimethyl polysiloxane                    | 0.5         |
| (9)  | N-methylpyrolidone                       | 10.0        |
| (10) | Citric acid                              | 4.0         |
| (11) | Glycerine                                | 0.5         |
| (12) | Polyoxyethylene (100) hardened castor oil ester | 1.0  |
| (13) | Hydrolyzed silk protein                  | 0.1         |
| (14) | Perfume                                  | Appropriate amount |
| (15) | Ion exchanged water                      | Balance     |

The acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

Example A5
Acidic Hair Dye (5)

|      |                                          | Blend ratio |
| ---- | ---------------------------------------- | ----------- |
| (1)  | Black 401                                | 0.2         |
| (2)  | Purple 401                               | 0.3         |
| (3)  | Yellow 4                                 | 0.1         |
| (4)  | Benzyl alcohol                           | 5.0         |
| (5)  | Succinoglycan                            | 1.5         |
| (6)  | Dimethyl polysiloxane                    | 0.5         |
| (7)  | N-methylpyrolidone                       | 13.5        |
| (8)  | Phosphoric acid                          | 0.8         |
| (9)  | Glycerine                                | 0.5         |
| (10) | Hydrolyzed elastin                       | 0.2         |
| (11) | Polyoxyethylene (100) hardened castor oil ester | 1.0  |
| (12) | Perfume                                  | Appropriate amount |
| (13) | Ion exchanged water                      | Balance     |

The acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

Example A6
Acidic Hair Dye (6)

|      |                                          | Blend ratio |
| ---- | ---------------------------------------- | ----------- |
| (1)  | Black 401                                | 0.2         |
| (2)  | Purple 401                               | 0.3         |
| (3)  | Yellow 4                                 | 0.1         |
| (4)  | 2-phenoxy ethanol                        | 5.0         |
| (5)  | Succinoglycan                            | 1.0         |
| (6)  | Dimethyl polysiloxane                    | 0.5         |
| (7)  | 1,3-butylene glycol                      | 9.5         |
| (8)  | Citric acid                              | 4.0         |
| (9)  | Polyoxyethylene (100) hardened castor oil ester | 1.0  |
| (10) | Quarternarized salt of hydrolyzed collagen | 0.1       |
| (11) | Perfume                                  | Appropriate amount |
| (12) | Ion exchanged water                      | Balance     |

The acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

Example A7
Acidic Hair Dye (7)

| | | Blend ratio |
|---|---|---|
| (1) | Black 401 | 0.2 |
| (2) | Purple 401 | 0.3 |
| (3) | Yellow 4 | 0.1 |
| (4) | Benzyl alcohol | 7.0 |
| (5) | Succinoglycan | 2.0 |
| (6) | Methylphenyl polysiloxane | 0.5 |
| (7) | N-methylpyrolidone | 12.0 |
| (8) | Citric acid | 4.0 |
| (9) | Glycerine | 0.5 |
| (10) | Quarternarized salt of hydrolyzed keratin | 0.1 |
| (11) | Polyoxyethylene (100) hardened castor oil ester | 1.0 |
| (12) | Perfume | Appropriate amount |
| (13) | Ion exchanged water | Balance |

The acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

Example A8
Acidic Hair Dye (8)

| | | Blend ratio |
|---|---|---|
| (1) | Black 401 | 0.2 |
| (2) | Purple 401 | 0.3 |
| (3) | Yellow 4 | 0.1 |
| (4) | Benzyl alcohol | 5.0 |
| (5) | Succinoglycan | 2.0 |
| (6) | Cross-linked sodium polyacrylate | 0.2 |
| (&) | Poly ether modified polysiloxane | 0.5 |
| (8) | 1,3-butylene glycol | 10.0 |
| (9) | Citric acid | 4.0 |
| (10) | Glycerine | 0.5 |
| (11) | Quarternarized salt of hydrolyzed soybean protein | 0.2 |
| (12) | Polyoxyethylene (100) hardened castor oil ester | 1.0 |
| (13) | Perfume | Appropriate amount |
| (14) | Ion exchanged water | Balance |

The acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

Example A9
Acidic Hair Dye (9)

| | | Blend ratio |
|---|---|---|
| (1) | Black 401 | 0.2 |
| (2) | Purple 401 | 0.3 |
| (3) | Yellow 4 | 0.1 |
| (4) | Benzyl alcohol | 7.0 |
| (5) | Succinoglycan | 2.0 |
| (6) | Cross-linked sodium polyacrylate | 0.2 |
| (7) | Polyether modified polysiloxane | 0.5 |
| (8) | Dipropylene glycol | 13.0 |
| (9) | Glycolic acid | 2.0 |
| (10) | 1,3-butylene glycol | 0.5 |
| (11) | Sodium chondroitinsulfate | 0.1 |
| (12) | Polyoxyethylene (100) hardened castor oil ester | 1.0 |
| (13) | Hydrolyzed elastin | 0.1 |
| (14) | Perfume | Appropriate amount |
| (15) | Ion exchanged water | Balance |

The acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

Example A10
Acidic Hair Dye (10)

| | | Blend ratio |
|---|---|---|
| (1) | Black 401 | 0.2 |
| (2) | Purple 401 | 0.3 |
| (3) | Yellow 4 | 0.1 |
| (4) | Benzyl alcohol | 5.0 |
| (5) | Succinoglycan | 3.0 |
| (6) | Amino modified polysiloxane | 0.5 |
| (7) | N-methylpyrolidone | 12.0 |
| (8) | Citric acid | 4.0 |
| (9) | Sodium pyrolidonecarboxylate | 0.5 |
| (10) | Hydrolyzed silk protein | 0.1 |
| (11) | Polyoxyethylene (100) hardened castor oil ester | 1.0 |
| (12) | Perfume | Appropriate amount |
| (13) | Ion exchanged water | Balance |

The acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

Example A11
Acidic Hair Dye (A11)

| | | Blend ratio |
|---|---|---|
| (1) | Black 401 | 0.2 |
| (2) | Purple 401 | 0.3 |
| (3) | Yellow 4 | 0.1 |
| (4) | Benzyl alcohol | 5.0 |
| (5) | Succinoglycan | 2.0 |
| (6) | Dimethyl polysiloxane | 0.5 |
| (7) | Tetrahydrofurfuryl alcohol | 13.0 |
| (8) | Citric acid | 3.0 |
| (9) | Propylene glycol | 5.0 |
| (10) | Hydrolyzed keratin | 0.1 |
| (11) | Polyoxyethylene (100) hardened castor oil este | 1.0 |
| (12) | Perfume | Appropriate amount |
| (13) | Ion exchanged water | Balance |

The acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

Example A12
Acidic Hair Dye (12)

|      |                                              | Blend ratio        |
| ---- | -------------------------------------------- | ------------------ |
| (1)  | Black 401                                    | 0.2                |
| (2)  | Purple 401                                   | 0.3                |
| (3)  | Yellow 4                                     | 0.1                |
| (4)  | Benzyl alcohol                               | 8.0                |
| (5)  | Succinoglycan                                | 5.0                |
| (6)  | Polyether modified polysiloxane              | 0.5                |
| (7)  | Dimethyl polysiloxane                        | 0.5                |
| (8)  | Tetrahydrofurfuryl alcohol                   | 12.0               |
| (9)  | Citric acid                                  | 3.0                |
| (10) | Glycerine                                    | 0.5                |
| (11) | Carboxymethyl cellulose                      | 0.1                |
| (12) | Polyoxyethylene (100) hardened castor oil ester | 1.0             |
| (13) | Hydrolyzed keratin                           | 0.2                |
| (14) | Perfume                                      | Appropriate amount |
| (15) | Ion exchanged water                          | Balance            |

The acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

Example A13
Acidic Hair Dye (13)

|      |                                              | Blend ratio        |
| ---- | -------------------------------------------- | ------------------ |
| (1)  | Black 401                                    | 0.2                |
| (2)  | Purple 401                                   | 0.3                |
| (3)  | Orange 205                                   | 0.2                |
| (4)  | Benzyl alcohol                               | 8.0                |
| (5)  | Succinoglycan                                | 10.0               |
| (6)  | Isopropyl alcohol                            | 21.6               |
| (7)  | Hexylene diglycol                            | 4.5                |
| (8)  | Phosphoric acid                              | 0.8                |
| (9)  | Polyoxyethylene (100) hardened castor oil ester | 1.0             |
| (10) | Hydrolyzed keratin                           | 0.2                |
| (11) | Perfume                                      | Appropriate amount |
| (12) | Ion exchanged water                          | Balance            |

The acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

Example A14
Acidic Hair Dye (14)

|      |            | Blend ratio |
| ---- | ---------- | ----------- |
| (1)  | Orange 205 | 0.2         |
| (2)  | Red 227    | 0.1         |

-continued

|      |                                              | Blend ratio        |
| ---- | -------------------------------------------- | ------------------ |
| (3)  | Purple 401                                   | 0.05               |
| (4)  | Green 204                                    | 0.05               |
| (5)  | Benzyl alcohol                               | 10.0               |
| (6)  | Succinoglycan                                | 2.3                |
| (7)  | Ethanol                                      | 16.0               |
| (8)  | 1,3-butylene glycol                          | 5.0                |
| (9)  | Phosphoric acid                              | 1.0                |
| (10) | Polyoxyethylene (100) hardened castor oil ester | 1.0             |
| (11) | Hydrolyzed keratin                           | 0.1                |
| (12) | Perfume                                      | Appropriate amount |
| (13) | Ion exchanged water                          | Balance            |

The acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

Example A15
Color Rinse Type Acidic Hair Dye (1)

|      |                                              | Blend ratio        |
| ---- | -------------------------------------------- | ------------------ |
| (1)  | Black 401                                    | 0.02               |
| (2)  | Purple 401                                   | 0.03               |
| (3)  | Yellow 4                                     | 0.01               |
| (4)  | Benzyl alcohol                               | 3.0                |
| (5)  | Succinoglycan                                | 0.005              |
| (6)  | Polyether modified polysiloxane              | 0.6                |
| (7)  | 1,3-butylene glycol                          | 9.5                |
| (8)  | Citric acid                                  | 0.6                |
| (9)  | Glycerine                                    | 0.5                |
| (10) | Octamethylcyclotetrasiloxane                 | 3.0                |
| (11) | Polyoxyethylene (100) hardened castor oil ester | 0.7             |
| (12) | 1,3-butylene glycol                          | 15.0               |
| (13) | Quarternarized hydrolyzed collagen protein   | 0.2                |
| (14) | Perfume                                      | Appropriate amount |
| (15) | Ion exchanged water                          | Balance            |

The color rinse type acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

Example A16
Color Rinse Type Hair Dye (2)

|      |                                              | Blend ratio |
| ---- | -------------------------------------------- | ----------- |
| (1)  | Black 401                                    | 0.02        |
| (2)  | Purple 401                                   | 0.03        |
| (3)  | Yellow 4                                     | 0.01        |
| (4)  | Benzyl alcohol                               | 3.0         |
| (5)  | Succinoglycan                                | 0.1         |
| (6)  | Polyether modified polysiloxane              | 0.2         |
| (7)  | Dimethyl polysiloxane                        | 0.5         |
| (8)  | Tetrahydrofurfuryl alcohol                   | 8.7         |
| (9)  | Citric acid                                  | 0.6         |
| (10) | Glycerine                                    | 0.5         |
| (11) | Octamethylcyclotetrasiloxane                 | 3.0         |
| (12) | Polyoxyethylene (100) hardened castor oil    | 0.7         |

-continued

|  |  | Blend ratio |
|---|---|---|
|  | ester |  |
| (13) | 1,3-butylene glycol | 15.0 |
| (14) | Xanthan gum | 0.5 |
| (15) | Bentonite | 0.3 |
| (16) | Quarternarized hydrolyzed silk protein | 0.2 |
| (17) | Perfume | Appropriate amount |
| (18) | Ion exchanged water | Balance |

The color rinse type acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

Example A17
Color Rinse Type Hair Dye (3)

|  |  | Blend ratio |
|---|---|---|
| (1) | Black 401 | 0.02 |
| (2) | Purple 401 | 0.03 |
| (3) | Yellow 4 | 0.01 |
| (4) | Benzyl alcohol | 3.0 |
| (5) | Succinoglycan | 0.5 |
| (6) | Polyether modified polysiloxane | 0.2 |
| (7) | Amino modified polysiloxane | 0.5 |
| (8) | Tetrahydrofurfuryl alcohol | 8.5 |
| (9) | Citric acid | 0.6 |
| (10) | Glycerine | 0.5 |
| (11) | Octamethylcyclotetrasiloxane | 3.0 |
| (12) | Stearyltrimethylammonium chloride | 0.1 |
| (13) | Polyoxyethylene (100) hardened castor oil ester | 0.7 |
| (14) | 1,3-butylene glycol | 15.0 |
| (15) | Xanthan gum | 0.5 |
| (16) | Hydrolyzed keratin protein | 0.2 |
| (17) | Cross-linked sodium polyacrylate | 0.3 |
| (18) | Perfume | Appropriate amount |
| (19) | Ion exchanged water | Balance |

The color rinse type acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

Example A18
Color Rinse Type Hair Dye (4)

|  |  | Blend ratio |
|---|---|---|
| (1) | Black 401 | 0.02 |
| (2) | Purple 401 | 0.03 |
| (3) | Yellow 4 | 0.01 |
| (4) | Benzyl alcohol | 4.5 |
| (5) | Succinoglycan | 0.5 |
| (6) | Amino modified polysiloxane | 0.6 |
| (7) | Tetrahydrofurfuryl alcohol | 8.0 |
| (8) | Citric acid | 0.6 |
| (9) | Glycerine | 0.5 |
| (10) | Octamethylcyclotetrasiloxane | 3.0 |
| (11) | Polyoxyethylene (100) hardened castor oil ester | 0.7 |
| (12) | 1,3-butylene glycol | 15.0 |
| (13) | Bentonite | 0.3 |
| (14) | Hydrolyzed soybean protein | 0.1 |
| (15) | Perfume | Appropriate amount |
| (16) | Ion exchanged water | Balance |

The color rinse type acidic hair dye prepared with a conventional method using the recipe above exhibited superior stability, adequate viscosity, no peculiar smell, no dripping from the hair on the head, superior dyeability and dyeing homogeneity, superior color retention, no stickiness at the time of application and adequate ease of washing off.

(B) Examples in Which the Hair Dye Composition of the Present Invention is an Oxidation Hair Dye Composition

[Evaluation of the Hair Dye Composition]

The compositions for oxidation hair dyes prepared by the following recipes were evaluated by (1) dye finish testing, (2) fastness testing and (3) hair damage testing.

Hair Dyeing Method

Formulations (I) and (II) of an oxidation hair dye of the following recipe were mixed together with a ratio of 15 g:15 g, applied on hair (5 g of gray hair), and let stand for 20 minutes. This hair was then thoroughly rinsed with warm water at 40° C. and dried for 15 minutes at 40° C. (this hair dyeing method is common for all the test systems).

(1) Dye Finish Testing

The dye finish of the oxidation hair dye prepared according to the following recipe was evaluated by using 5 types of hair strands and comparing the dye finish of this oxidation hair dye with that of an oxidation hair dye with the same recipe except for the absence of succinoglycan (comparative example).

Evaluation Criteria o: The example has superior dye-affinity than the comparative example.

Δ: The example's dye-affinity is comparable to that of the comparative example.

x: The example is inferior to the comparative example.

(2) Fastness Testing:

The oxidation hair dye prepared according to the following recipes (example as well as corresponding comparative example which has the aforementioned relationship with the example) was used to dye 5 types of hair strands and the fastness was compared in the following manner.

(a) Comparison of Shampooing Resistance

The dyed hair was shampooed twice with a 2% sodium laurate solution (40° C., 10 minutes) and then dried in a thermostatic bath (40° C. 15 minutes). This operation was repeated 10 times and then the color change of the dyed hair (fading and discoloration) was observed and evaluated using the following criteria.

Evaluation Criteria o: The example is superior to the comparative example.

Δ: The example is comparable to the comparative example.

x: The example is inferior to the comparative example.

(b) Evaluation of Light Resistance

The dyed hair was exposed to sunlight for 60 days (accumulated amount of sunlight: 27,000 cal/cm) and, using the dyed hair which did not receive this sunlight exposure treatment as a control, the changes in the dyed hair (fading and discoloration) were observed and evaluated using the following criteria.

Evaluation Criteria
○: The example is superior to the comparative example.
Δ: The example is comparable to the comparative example.
x: The example is inferior to the comparative example.

(3) Hair Damage Testing

The degree of hair cuticle damage due to the use of the oxidation hair dye prepared according to the following recipe was evaluated by using 5 types of hair strands and comparing this oxidation hair dye and an oxidation hair dye with the same recipe except for the absence of succinoglycan (comparative example) by means of electron microscopic observation (magnification: 3,000 times) of the hair surface before and after the dyeing.

Evaluation Criteria
○: The same as before the dyeing. No damage observed.
Δ: Slight damage of cuticles such as protuberances, cracks and detachment is observed.
x: Considerable damage of cuticles such as protuberances, cracks and detachment is observed.

(4) Testing of Stability Over Time

Samples of the oxidation hair dye prepared according to the following recipes (Examples B3, B4 and B5) were put into a 50-ml screw tube and each sample was stored under a specific temperature condition (−5° C., 0° C., room temperature (RT) or 50° C.) to carry out a month of testing of stability over time.

This evaluation of the stability over time was carried out in a comprehensive manner by observing changes in the outer appearance, changes in the viscosity and the amount of free ammonia.

Evaluation Criteria
○: No change was observed after 1 month.
Δ: Changes to a degree which does not affect the actual use were observed.
x: Changes to a degree which would make the actual use difficult were observed.

Example B1

Oxidation Hair Dye (1)

Blend ratio [wt % of the total composition (this applies to ratios hereafter)]

(Formulation (I))

| Paraphenylenediamine | 1.0 |
|---|---|
| Propylene glycol | 10.0 |
| Sodium edetate | 0.3 |
| Sodium sulfite | 0.5 |
| Sodium ascorbate | 0.5 |
| Succinoglycan | 1.0 |
| Aqueous ammonia | Amount to achieve pH 10 |
| Ion exchanged water | Balance |

(Formulation (II))

| 30% aqueous hydrogen peroxide | 6.0 |
|---|---|
| Ion exchanged water | Balance |

<Preparation Method>

Both formulations (I) and (II) were prepared by mixing the blend ingredients.

Using the oxidation hair dye (1) the aforementioned (1) dye finish testing, (2) fastness testing [(a) evaluation of shampoo resistance, (b) evaluation of light resistance] and (3) hair damage testing were carried out. The testing results are shown Table 5 (dye finish testing), Table 6 (fastness testing) and Table 7 (hair damage testing).

TABLE 5

(Dye finish testing)

| Strand | Evaluation |
|---|---|
| a | ○ |
| b | ○ |
| c | ○ |
| d | Δ |
| e | ○ |

TABLE 6

(Fastness testing)

| | Evaluation | |
|---|---|---|
| Strand | Sunlight | Shampoo |
| a | ○ | ○ |
| b | ○ | ○ |
| c | ○ | ○ |
| d | Δ | ○ |
| e | Δ | Δ |

TABLE 7

(Hair damage testing)

| | Evaluation | |
|---|---|---|
| Strand | Example B1 | Comparative example B1 |
| a | ○ | X |
| b | ○ | X |
| c | Δ | Δ |
| d | ○ | X |
| e | ○ | X |

The visual observation during the aforementioned dye finish testing indicated that each strand had superior gloss as well.

These results indicated that, due to the addition of succinoglycan, the oxidation hair dye of the present invention was superior in terms of the fastness of the hair dye, which had been an important issue in conventional hair dyes, and hardly any hair damage was observed. These results also indicated that the gloss of hair can be further improved by this acidic hair dye.

Example B2

Oxidation Hair Dye (2)

| | Blend ratio (wt %) |
|---|---|
| (Formulation (I)) | |
| Paraphenylenediamine | 1.0 |
| Resorcinol | 0.8 |
| Propylene glycol | 10.0 |
| Sodium edetate | 0.3 |
| Sodium sulfite | 0.5 |
| Sodium ascorbate | 0.5 |
| Succinoglycan | 1.0 |
| Aqueous ammonia | Amount to achieve pH 10 |
| Ion exchanged water | Balance |

| | Blend ratio (wt %) |
|---|---|
| (Formulation (II)) | |
| 30% aqueous hydrogen peroxide | 6.0 |
| Ion exchanged water | Balance |

<Preparation method>

Both formulations (I) and (II) were prepared by mixing the blend ingredients.

Using the oxidation hair dye (2) of Example B2, the aforementioned (1) dye finish testing, (2) fastness testing [(a) evaluation of shampoo resistance, (b) evaluation of light resistance] and (3) hair damage testing were carried out. The results obtained were good and comparable to those for oxidation hair dye (1) of Example B1 described above.

A type of oxidation hair dye (2) of Example B2 to whose formulation (I) 1.0 wt % of polypeptide (hydrolyzed collagen) was added exhibited comparable results in the aforementioned dye finish testing. But this type of oxidation hair dye, which contained a polypeptide, excelled in the fastness testing, particularly the shampooing resistance testing (all the strands were evaluated "○" and each strand exhibited much superior results than those of Comparative example B2).

This result shows that the oxidation hair dye of the present invention which contains a polypeptide is superior particularly in the fastness of dyeing against shampoos.

Example B3

Cream-type Oxidation Hair Dye

| | Blend ratio (wt %) |
|---|---|
| (Formulation (I)) | |
| Paraphenylenediamine | 1.5 |
| Metaphenylenediamine | 1.0 |
| Polyoxyethylenealkyl ether salt | 3.0 |
| Cetostearyl alcohol | 15.0 |
| Liquid paraffin | 3.0 |
| Succinoglycan | 2.0 |
| Hydrolyzed keratin | 1.0 |
| Perfume | Appropriate amount |
| Aqueous ammonia | Amount to achieve pH 10 |
| Ion exchanged water | Balance |
| (Formulation (II)) | |
| 30% aqueous hydrogen peroxide | 6.0 |
| Edetic acid | 0.5 |
| Cetanol | 2.0 |
| Sodium alkylate | 0.5 |
| Sodium stannate | 0.1 |
| Ion exchanged water | Balance |

<Preparation Method>

Preparation was carried out in the same manner as in the aforementioned Example B2.

The aforementioned (4) stability-over-time testing was carried out on this oxidation hair dye of the present invention. The result is shown in the following Table 8. The oxidation hair dye of Comparative example B3 in Table 8 is an oxidation hair dye prepared from the recipe of the oxidation hair dye of Example B3 except for the fact that succinoglycan is replaced by dextrin pullulan.

TABLE 8

(Stability-over-time testing)

| | Evaluation | |
|---|---|---|
| Temperature | Example B3 | Comparative example B3 |
| −5° C. | ○ | ○ |
| 0° C. | ○ | ○ |
| RT | ○ | ○ |
| 50° C. | ○ | x |

This result shows that, by the addition of succinoglycan, the oxidation hair dye of the present invention has made an improvement in stability over time, which has been a problem.

This oxidation hair dye of the present invention in Example B3 was also evaluated in tests other than the one described above and in each test it produced comparable results to the aforementioned oxidation hair dye of the present invention in Example B1.

Example B4

Gel-type Oxidation Hair Dye

| | Blend ratio (wt %) |
|---|---|
| (Formulation (I)) | |
| Paraphenylenediamine | 20.0 |
| Paraamino phenol | 0.5 |
| Resorcinol | 0.5 |
| Polyoxyethylene alkylphenyl ether | 20.0 |
| Oleic acid | 5.0 |
| Polyethylene glycol | 20.0 |
| Sodium sulfite | 0.5 |
| Succinoglycan | 1.0 |
| Perfume | Appropriate amount |
| Monoethanol amine | Amount to achieve pH 10 |
| Ion exchanged water | Balance |
| (Formulation (II)) | |
| 30% aqueous hydrogen peroxide | 6.0 |
| Edetic acid | 0.5 |
| Cetanol | 2.0 |
| Sodium alkylate | 0.5 |
| Sodium stannate | 0.1 |
| Ion exchanged water | Balance |

<Preparation Method>

Preparation was carried out in the same manner as in the aforementioned example.

This oxidation hair dye of the present invention in Example B4 was evaluated by the aforementioned tests (1)–(3) (dye finish testing, fastness testing and hair damage testing) and the results of each test were comparable to that of the oxidation hair dye of the present invention in Example B1. The result of the aforementioned test (4) (stability-over-time testing) was comparable to that of the aforementioned oxidation hair dye of the present invention in Example B3.

Example B5
Shampoo-type Oxidation Hair Dye

|  | Blend ratio (wt %) |
|---|---|
| (Formulation (I)) | |
| Paraphenylene diamine | 0.8 |
| Orthoamino phenol | 1.0 |
| Resorcinol | 1.5 |
| Polyoxyethylene alkylphenyl ether | 22.0 |
| Oleic acid | 3.0 |
| Isopropyl alcohol | 10.0 |
| Succinoglycan | 0.5 |
| Aqueous ammonia | Amount to achieve pH 10 |
| Perfume | Appropriate amount |
| Ion exchanged water | Balance |
| (Formulation (II)) | |
| 30% aqueous hydrogen peroxide | 6.0 |
| Edetic acid | 0.5 |
| Cetanol | 2.0 |
| Sodium alkylate | 0.5 |
| Sodium stannate | 0.1 |
| Ion exchanged water | Balance |

<Preparation method>

Preparation was carried out in the same manner as in the aforementioned example.

This oxidation hair dye of the present invention in Example B5 was evaluated by the aforementioned tests (1)–(3) (dye finish testing, fastness testing and hair damage testing) and the results in each test were comparable to that of the aforementioned oxidation hair dye of the present invention in Example B1. The result of the aforementioned test (4) (stability-over-time testing) was comparable to that of the aforementioned oxidation hair dye of the present invention in Example B3.

Industrial Applicability of the Invention

As described thus far, the hair dye composition pertaining to the present invention has excellent characteristics as described below, is useful as a hair dye and is particularly suitable for use as an acidic hair dye and an oxidation hair dye.

Specifically, firstly, the hair dye composition of the present invention has a superior dyeability and excellent fastness of dyeing against sunlight and hair washing, causes very little damage on hair, can improve the hair gloss and exhibits a superior stability over time.

Secondly, the hair dye composition of the present invention, even in a strongly acidic region, exhibited superior stability, adequate viscosity, no peculiar smell, no dripping from the hair on the head, superior dyeability and dyeing homogeneity, superior color retention, no stickiness at the time of application and adequate ease of washing off.

We claim:

1. A hair dye composition comprising oxidation hair dye and succinoglycan, wherein the hair dye composition is an oxidation hair dye composition.

2. The hair dye composition of claim 1 wherein the oxidation hair dye composition is an oxidation hair dye composition to which a polypeptide and/or its derivative are additionally blended in.

3. A method of dyeing hair comprising applying to the hair a hair dye composition comprising a mixture of succinoglycan and hair dye in an amount effective to dye hair.

4. The method of dyeing hair according to claim 3, wherein said hair dye is an oxidation hair dye composition.

5. The method of dyeing hair according to claim 3, wherein said hair dye is an acidic hair dye composition.

* * * * *